United States Patent
Gloux et al.

(10) Patent No.: US 7,319,150 B2
(45) Date of Patent: Jan. 15, 2008

(54) METHOD FOR PREPARING STYRYL PYRAZOLE, ISOXAZOLE AND ISOTHIAZOLE DERIVATIVES

(75) Inventors: Damien Gloux, Montpellier (FR); Marc Criton, Montpellier (FR); Jean-Louis Montero, Valflaunes (FR)

(73) Assignees: Laboratoires Mayoly Spindler (FR); Centre National De La Recherche Scientifique (FR); Universite De Montpellier 2 (FR)

( * ) Notice: Subject to any disclaimer, the term of this patent is extended or adjusted under 35 U.S.C. 154(b) by 352 days.

(21) Appl. No.: 10/522,927

(22) PCT Filed: Jul. 24, 2003

(86) PCT No.: PCT/FR03/02341

§ 371 (c)(1),
(2), (4) Date: Aug. 4, 2005

(87) PCT Pub. No.: WO2004/011444

PCT Pub. Date: Feb. 5, 2004

(65) Prior Publication Data

US 2006/0135580 A1     Jun. 22, 2006

(30) Foreign Application Priority Data

Jul. 26, 2002   (FR)   .................... 02 09483

(51) Int. Cl.
*C07D 233/64*   (2006.01)
*C07D 263/32*   (2006.01)
*C07D 277/24*   (2006.01)

(52) U.S. Cl. .................. 548/101; 548/201; 548/236; 548/374.1

(58) Field of Classification Search ............. 548/101, 548/201, 236, 374.1
See application file for complete search history.

(56) References Cited

FOREIGN PATENT DOCUMENTS

EP   0 245 825 A   11/1987

OTHER PUBLICATIONS

Da Re P et al., "Structure-activity relationships in centrally stimulating xanthone derivatives. Part IV.—Dibenzo-'A, e!-cycloheptatrien-5-one and 5-ol derivatives", *Chimie Therapeutique*, No. 1, 1973, pp. 53-56.
Herz W. et al., "2-Vinylpyrrole and homologs", *Journal of the American Chemical Society*, vol. 76, No. 2, Jan. 20, 1954, pp. 576-578.

*Primary Examiner*—Taofiq Solola
(74) *Attorney, Agent, or Firm*—Alston & Bird LLP

(57) ABSTRACT

The invention concerns a method for synthesizing styryl isoxazole, styryl pyrazole and styryl isothazole derivatives in a synthesis step followed by a recrystallization in a basic alcohol medium.

13 Claims, No Drawings

METHOD FOR PREPARING STYRYL PYRAZOLE, ISOXAZOLE AND ISOTHIAZOLE DERIVATIVES

FIELD OF THE INVENTION

The present invention relates to a novel method for synthesizing styryl isoxazole, styryl pyrazole and styryl isothiazole derivatives.

The subject of the present invention is in particular a method for producing compounds of the styryl isoxazole, styryl pyrazole and styryl isothiazole family in a synthesis step followed by recrystallization from a basic alcoholic medium, serving as a dehydration and a purification. This method relates in particular to the production of (E)-5-[2-(3,5-di-tert-butyl-4-hydroxyphenyl)vinyl]-3-methylisoxazole also called 5-[β-(4'-hydroxy-3',5'-bis-(1, 1-dimethylethyl)phenyl)ethenyl]-3-methylisoxazole.

BACKGROUND OF THE INVENTION

Styryl isoxazole, styryl pyrazole and styryl isothiazole compounds, and in particular (E)-5-[2-(3,5-di-tert-butyl-4-hydroxyphenyl)vinyl]-3-methylisoxazole, have been described in patent EP 0 245 825. These compounds, which are 5-lipoxygenase and cyclooxygenase inhibitors, can be used in a pharmaceutical composition. They also have sunscreen properties. In particular, they are capable of entering into the composition of pharmaceutical formulations for the treatment of inflammation, arthritis, ulcers, allergies, asthma, psoriasis, cardiovascular states in mammals. They are also used in compositions for protecting against ultraviolet light.

The synthesis of styryl isoxazole derivatives which is described in patent EP 0 245 825 may be carried out according to three approaches. In particular, in the case of (E)-5-[2-(3,5-di-tert-butyl-4-hydroxyphenyl)vinyl]-3-methylisoxazole, the following three synthesis schemes are possible:

I Wittig reaction between the aldehyde (3,5-di-tert-butyl-4-hydroxybenzaldehyde) and 3,5-di-methylisoxazole triphenylphosphonium

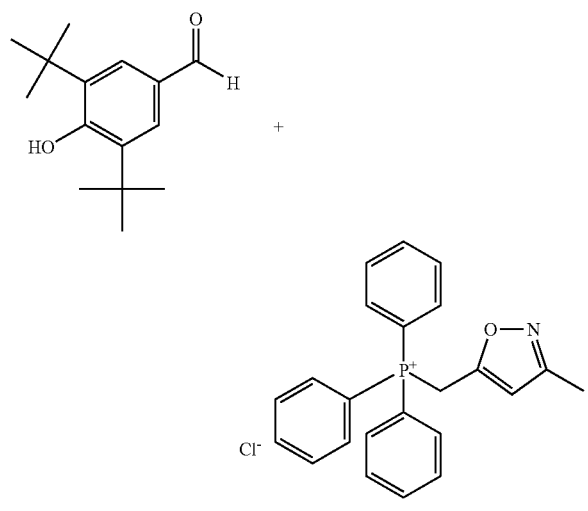

II Two-step method comprising:
A reaction between the aldehyde (3,5-di -tert-butyl-4-hydroxybenzaldehyde) and the lithium salt of 3,5-dimethylisoxazole followed by chromatography on a silica gel column.
A second step comprising the treatment of the product resulting from the first step with hydro-chloric acid in methanol to give, after purification on a silica gel column, the desired compound with a yield of 49%.

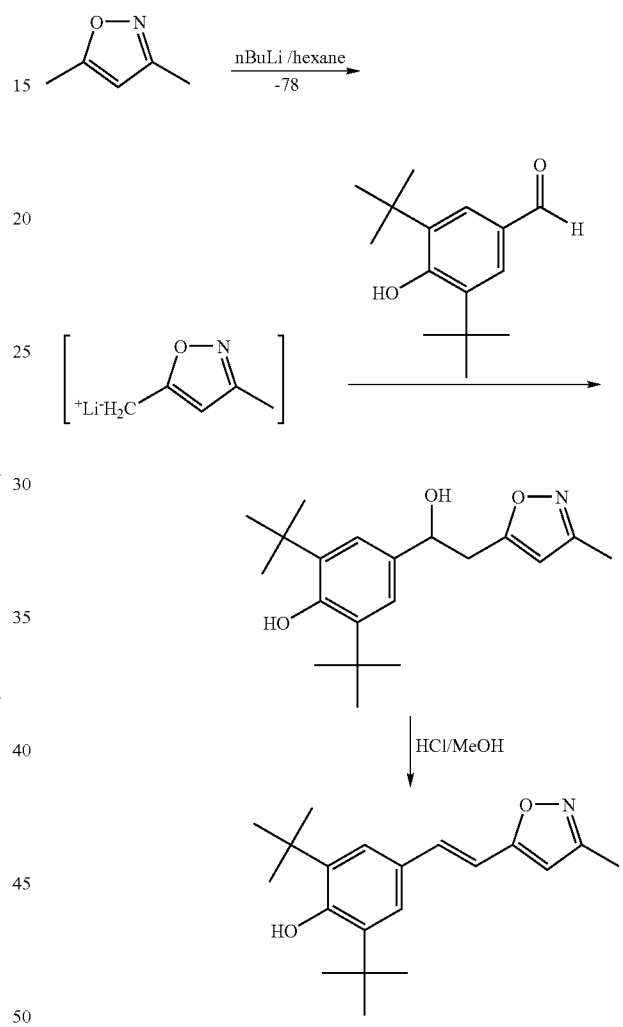

III A third approach consists in reacting the aldehyde (3,5-di-tert-butyl-4-hydroxybenzaldehyde) with a 3-carboxylate derivative of isoxazole. After condensation, a dehydration and a decarboxylation are carried out.

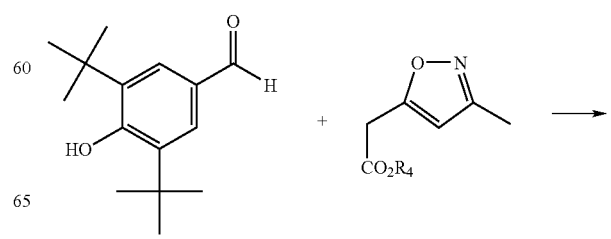

-continued

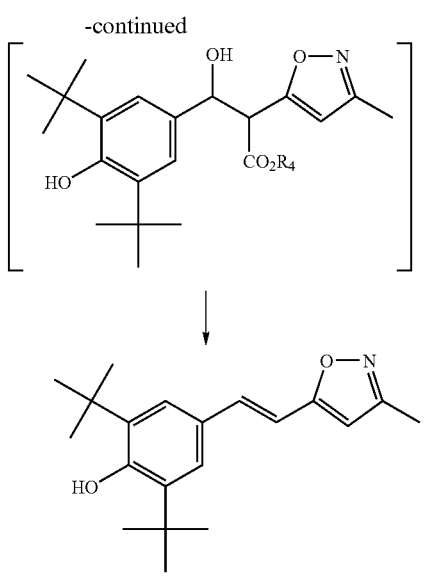

The same synthesis schemes make it possible to obtain the styryl pyrazole and styryl isothiazole derivatives.

While the prior art methods make it possible to obtain the styryl isoxazole, styryl pyrazole and styryl isothiazole derivatives, they have the disadvantage of requiring the use of several steps and/or of purifications by chromatography in order to obtain a pure product.

SUMMARY OF THE INVENTION

The applicant set itself the objective of developing a method for preparing styryl isoxazole, styryl pyrazole and styryl isothiazole derivatives comprising a limited number of steps and making it possible to obtain a product having satisfactory purity without the need to use complicated and/or expensive purification steps.

The method of synthesis according to the invention applies to the preparation of compounds corresponding to formula (I) below

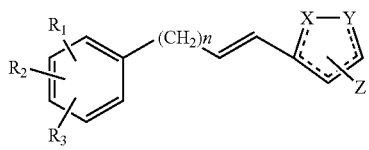
(I)

in which:

$R_1$, $R_2$, $R_3$, at the 2, 3, 4, 5 or 6 position of the phenyl ring, which are identical or different, are chosen from: a hydrogen atom; $C_1$-$C_6$ alkyls; $C_2$-$C_6$ alkenyls; $C_2$-$C_6$ alkynyls; halogens, $C_1$-$C_6$ haloalkyls; —OH; the groups —OR', —SH, —SR', —SeH, —SeR', —C(O)R', —NHC(O)R', —C(S)R', —NHC(S)R', —CN in which R' represents a group chosen from $C_1$-$C_6$ alkyls, $C_2$-$C_6$ alkenyls, $C_2$-$C_6$ alkynyls; the groups —C(O)OR", —OC(O)R", —NR"R'" in which R" and R'", which are identical or different, represent a group chosen from a hydrogen atom, $C_1$-$C_6$ alkyls, $C_2$-$C_6$ alkenyls, $C_2$-$C_6$ alkynyls;

X and Y represent a pair of atoms chosen from: ($NR_4$, N) (pyrazole ring), (O, N) (isoxazole ring), (S, N) (isothiazole ring), $R_4$ being chosen from: a hydrogen atom; $C_1$-$C_6$ alkyls; the groups $CH_2$—$OR_5$, the groups $C(O)OR_5$ in which $R_5$ is chosen from a hydrogen atom, a $C_1$-$C_6$ alkyl group, a benzyl group;

the heterocycle is linked to the phenyl ring via its 3- or 5-position in the case of the pyrazole ring, via its 5-position in the case of the isoxazole and isothiazole rings;

n represents an integer chosen from 0, 1, 2, 3, 4, 5 and 6;

Z, at the 3- or 4-position of the isoxazole, pyrazole or isothiazole ring, represents a group chosen from: a hydrogen atom; $C_1$-$C_6$ alkyls; $C_2$-$C_6$ alkenyls; $C_2$-$C_6$ alkynyls; halogens, $C_1$-$C_6$ haloalkyls; —OH; the groups —OR', —SH, —SR', —SeH, —SeR', —C(O)R', —NHC(O)R', —C(S)R', —NHC(S)R', —CN in which R' represents a group chosen from $C_1$-$C_6$ alkyls, $C_2$-$C_6$ alkenyls, $C_2$-$C_6$ alkynyls; the groups —C(O)OR", —OC(O)R", —NR"R'" in which R" and R'", which are identical or different, represent a group chosen from a hydrogen atom, $C_1$-$C_6$ alkyls, $C_2$-$C_6$ alkenyls, $C_2$-$C_6$ alkynyls.

The terms alkyl, alkenyl and alkynyl used in the present invention designate either linear, branched or cyclic radicals.

The heterocycle represented by the formula below:

represents according to the invention a group chosen from:

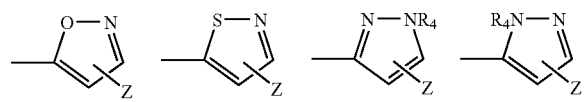

Preferably, the method according to the present invention applies to the preparation of the products corresponding to formula (I) above, in which one or more of the conditions below are met:

$R_1$, $R_2$, $R_3$ are at the 3-, 4- or 5-position of the phenyl ring;

$R_1$, $R_2$, $R_3$ are chosen from: a hydrogen atom; $C_1$-$C_6$ alkyls; halogens; $C_1$-$C_6$ haloalkyls; —OH; the groups —OR', in which R' represents a group chosen from $C_1$-$C_6$ alkyls; the groups —OC(O)R", in which R" represents a group chosen from a hydrogen atom, $C_1$-$C_6$ alkyls;

X=O; Y=N;

n=0;

Z is at the 3-position of the heterocycle, Z represents a group chosen from: $C_1$-$C_6$ alkyls; halogens; $C_1$-$C_6$ haloalkyls.

Advantageously, at least one of the conditions below is met:

the heterocycle represented by formula:

is a Z-substituted derivative of 5-isoxazole;

$R_1$ at the 3-position is a tert-butyl group;

$R_2$ at the 4-position is a hydroxyl group;

$R_3$ at the 5-position is a tert-butyl group;

Z at the 3-position is a methyl group.

Still more preferably, the invention applies to the preparation of (E)-5-[2-(3,5-di-tert-butyl-4-hydroxyphenyl)vinyl]-3-methylisoxazole.

The method which is the subject of the present invention is characterized in that it comprises at least one step consisting in treating the product corresponding to formula (II) below in which $R_1$, $R_2$, $R_3$, X, Y, Z and n have the same definition as in formula (I) above, in alcohol in the presence of a base to give the product of formula (I):

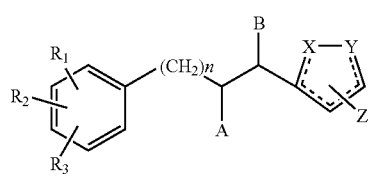

(II)

A and B being chosen such that one of A and B is H, the other being —OH.

In the case of the derivatives of formula (I) in which n=0, the method is similar to that developed by Warnert Lambert in patent EP 0 245 825 in that it comprises the passage via a common intermediate, but it differs therefrom in the number of steps, the treatment and the purification. Indeed, the alcohol (II) is subjected to a treatment in a basic alcoholic medium with the double objective of: 1) dehydrating the hydroxyl (II), 2) crystallizing the product (I) and thereby removing the impurities in the mother liquors, which makes it possible to avoid a column chromatography. Recrystallization from an alcoholic medium can optionally complete this method in order to give the product (I).

Compared with the prior art methods, the method according to the invention is distinguishable by the following advantages: a better yield, a small number of steps, a better feasibility on an industrial scale.

Preferably, the compound of formula (II) corresponds to formula (IIa) below in which $R_1$, $R_2$, $R_3$, X, Y and Z have the same definition as in formula (I):

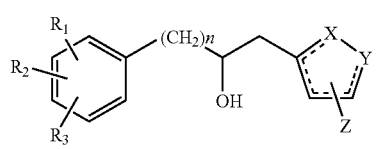

(IIa)

This variant represents the case where A=OH, B=H.

Advantageously, according to this variant of the invention, in the case where X=O and Y=N, the compound of formula (IIa) is prepared by a method consisting in reacting the aldehyde (III) and the lithium salt of the heterocycle (IVa):

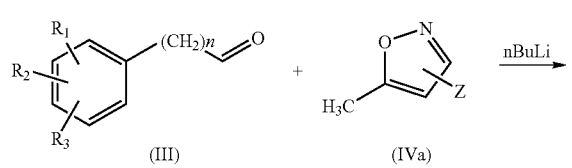

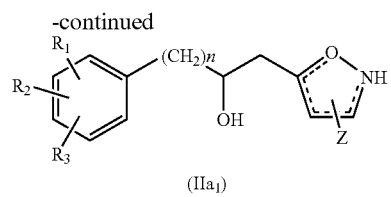

(IIa₁)

More particularly, in the case where n=0, the compound of formula (II) is prepared by a method consisting in reacting the aldehyde (IIIa) and the lithium salt of the 5-methylisoxazole derivative (IVa):

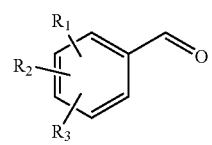

(IIIa)

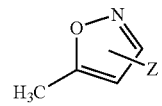

(IVa)

In the case where (X, Y) represents (S, N) or (NR₄, N), R₄ having the same definition as above, it is possible to have the target molecules (IIa) by reacting the phenyloxirane derivatives (V) with the lithium salt of the 5-isothiazole derivative (compound (IV) with X=S and Y=N) and with the lithium salt of the 5-pyrazole derivative (compound (IV) with (X, Y)=(NR₄, N)), according to the scheme below. Such syntheses are described in particular in: Ramacciotti, Alessio; Fiaschi, Rita; Napolitano, Elio; *Tetrahedron asymmetry;* 1996; 1101-1104:

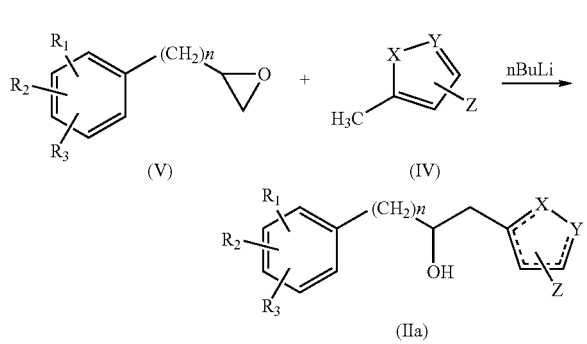

In the case where the compound of formula (II) corresponds to formula (IIb) below in which $R_1$, $R_2$, $R_3$, X, Y and Z have the same definition as in formula (I):

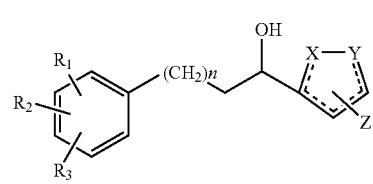

(IIb)

the product (IIb) is advantageously prepared by a method characterized in that:

in the case where X=O and Y=N, the aldehyde (VI) is reacted with a lithium salt of the heterocycle (VII):

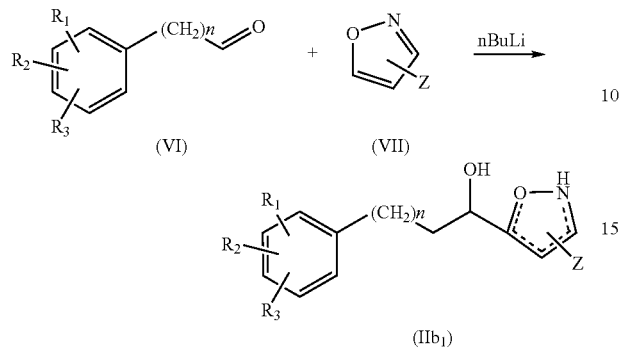

In the case where (X, Y) represents the pair of atoms (NR₄, N), R₄ being as defined above, the procedure is essentially carried out according to the scheme above using the method of protection described by Katritzky et al.: Alan R. Katritzky, Ping Lue and Kunihiko Akutagawa, *Tetrahedron* 45, 13 (1989), 4253-4262. The NH functional group of the pyrazole ring is protected with formaldehyde in order to avoid an N-alkylation. The resulting N-protected pyrazole is treated with n-butyllithium to give the lithium salt which, in the presence of aldehyde (VI), makes it possible to obtain the products of formula (IIb).

When X=S and Y=N, the product (IIb) is obtained according to the methods described in the following articles: A. J. Layton and E. Lunt J. Chem. Soc. C 1968, 611-614 and Ashton, Michael J and al. J. Med. Chem., 27, 10, 1984, 1245-1253. The isothiazole (VIII) is treated with n-butyllithium to give the lithium salt which in the presence of aldehyde (VI) makes it possible to obtain a 5-alkylation so as to correspond to the products of formula (IIb₂).

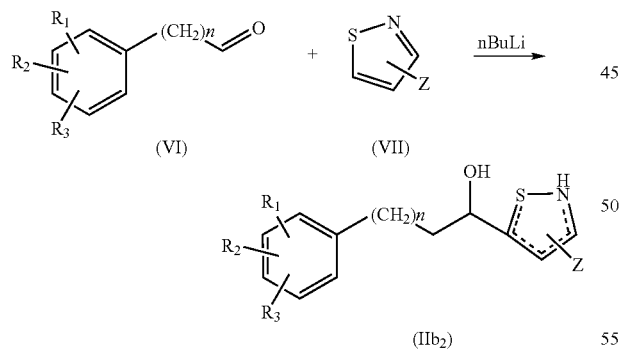

Advantageously, according to the invention, the methods above apply to the case where n=0.

Advantageously, according to the invention, the treatment of the product (II) in a basic alcoholic medium is characterized in that the alcohol in which the dehydration and the crystallization occur is ethanol, methanol or isopropyl alcohol. Advantageously still, the base which is added to the alcohol is sodium hydroxide in the form of an aqueous solution. Preferably, the aqueous sodium hydroxide solution is a solution having a concentration of between 0.1M and 5M, advantageously between 0.5M and 4M, still more advantageously between 1M and 3M.

Preferably, the method comprises the following steps: dissolution of the product (II) in alcohol under reflux; addition of the base until the compound (I) precipitates; addition of alcohol, still under reflux, until the precipitate is solubilized; cooling of the solution which causes crystallization of (I); filtration and washing of the crystals.

EXAMPLES

I Synthesis of (E)-5-[2-(3,5-di-tert-butyl-4-hydroxyphenyl)vinyl]-3-methylisoxazole 1.1 Reaction scheme:

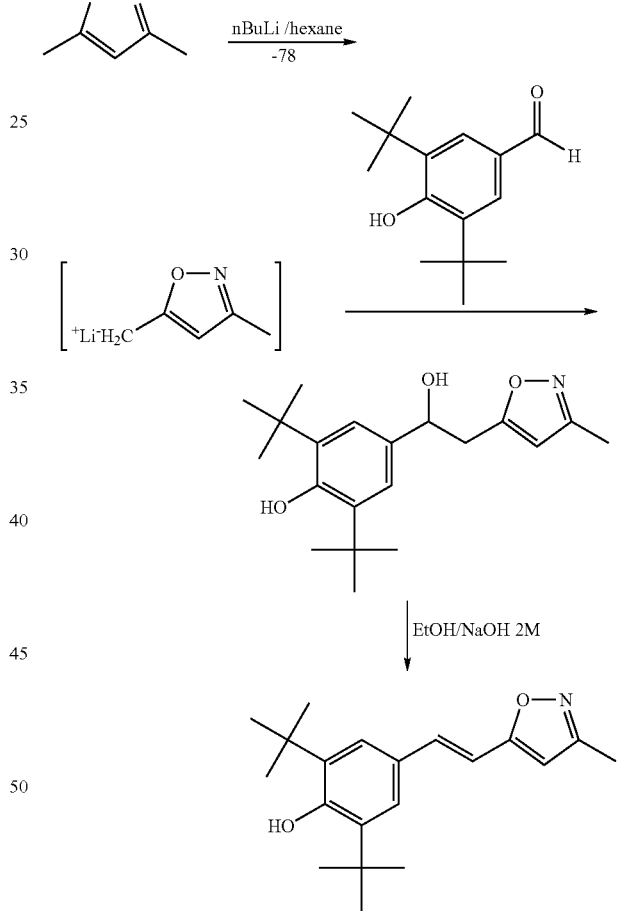

1.2 Reagents

The quantities of reagent are presented in table 1 below

TABLE 1

| Reagents | MW g/mol | Eq. | mmol | Quantity |
|---|---|---|---|---|
| 3,5-dimethylisoxazole | 7.12 (d = 0.99) | 2.1 | 257.13 | 25 g |
| n-butyllithium in hexane | 2.5 M | 2.1 | 257.413 | 100 ml |

TABLE 1-continued

| Reagents | MW g/mol | Eq. | mmol | Quantity |
|---|---|---|---|---|
| 3,5-di-tert-butyl-4-hydroxybenzaldehyde | 234.34 | | 122.577 | 28.724 g |
| THF | | | | 450 ml |

1.3 Procedure:

n-Butyllithium (100 ml) is added (over 45 minutes) dropwise to a solution of 3,5-dimethyl-isoxazole (25 g) in THF (200 ml) cooled to −78° C. After stirring for 1 hour at −78° C., 3,5-di-tert-butyl-4-hydroxybenzaldehyde (27.724 g) in solution in THF (250 ml) is added dropwise over 3 hours. At the end of the addition, the reaction mixture is left for 2 h 30 min with stirring at −78° C.

The progress of the reaction is monitored by thin-layer chromatography:

| Hexane/AcOEt | Rf aldehyde | Rf product (I) | Rf product (II) |
|---|---|---|---|
| 90/10 | 0.53 | 0.4 | 0.06 |
| 80/20 | | 0.6 | 0.21 |

When the aldehyde has been consumed, the following treatment is carried out:

concentration of the solvents (THF/hexane) by evaporation under vacuum, taking up of the medium in 200 ml of ethyl acetate, washing with twice 100 ml H$_2$O (pH aqueous phase 7), concentration under vacuum.

The second part of the method in accordance with the invention comprises the following steps:

a) Recrystallization/dehydration EtOH/NaOH 2M
- addition of 100 ml of ethanol, the mixture is heated under reflux
- addition of 2M NaOH until the product (I) precipitates (about 100 ml)
- addition of ethanol until solubilization of (I) is obtained
- filtration and washing of the crystals with 100 ml of H$_2$O and 100 ml of hexane.

(E)-5-[2-(3,5-Di-tert-butyl-4-hydroxyphenyl)vinyl]-3-methylisoxazole is obtained with an overall yield relative to the starting material which varies between 50% and 86%.

b) Optionally, a recrystallization with EtOH (8 ml/g) is then carried out

Mass obtained: 23.2 g/overall yield: 58%

II-Analysis of (E)-5-[2-(3,5-di-tert-butyl-4-hydroxyphenyl)vinyl]-3-methylisoxazole

2.1 Structural Study

Structural formula of (E)-5-[2-(3,5-di-tert-butyl-4-hydroxyphenyl)vinyl]-3-methylisoxazole:

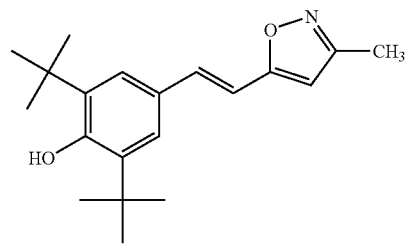

2.1.1 Infrared Spectrum

The infrared spectrum is performed between 4000 and 400 cm$^{-1}$ on a KBr pellet containing about 1% of (E)-5-[2-(3,5-di-tert-butyl-4-hydroxyphenyl)vinyl]-3-methylisoxazole The principal peaks observed are:

3500 cm$^{-1}$: $\nu_{O-H}$ 2850-2950 cm$^{-1}$: $\nu_{C-H}$ (tBu, CH$_3$, CH)

1640, 1570 and 1440 cm$^{-1}$: $\nu_{C=C}$ and $\nu_{C=N}$ 1230 and 1100 cm$^{-1}$: $\nu_{=C-O}$ 960 cm$^{-1}$: $\nu_{N-O}$ The IR spectrum is in conformity with the expected structure.

2.1.2 NMR Spectrum

The $^1$H NMR spectrum is performed on a solution in deuterated chloroform with a 200 MHz spectrometer.

Solvent peaks: TMS: 0 ppm; H$_2$O: 1.55 ppm; CHCl$_3$: 7.24 ppm.

The peaks for the compound are analyzed in table 2 below:

TABLE 2

| Chemical shift | Multiplicity | Integration | Attribution |
|---|---|---|---|
| 1.45 ppm | singlet | 18 H | 2 tBu |
| 2.3 ppm | singlet | 3 H | CH$_3$ at the 6-position |
| 5.4 ppm | singlet | 1 H | OH |
| 6.0 ppm | singlet | 1 H | H$_5$ |
| 6.75 ppm | doublet | 1 H | H$_4$ with J H$_3$—H$_4$ = 16 Hz |
| 7.2 ppm | doublet | 1 H | H$_3$ |
| 7.3 ppm | singlet | 2 H | H$_1$ and H$_2$ |

The NMR spectrum is in conformity with the expected structure.

2.1.3 Mass Spectrum

The mass spectrum is performed in "FAB positive" ionization with NBA (3-nitrobenzyl alcohol) for matrix.

The following ions are observed (table 3):

TABLE 3

| m/z | Attribution |
|---|---|
| 313 | M$^+$ |
| 314 | (M + H)$^+$ |
| 627 | (2 M + H)$^+$ |

The mass spectrum is in conformity with the expected structure.

2.1 Identification 2.2.1 Melting Point

The melting point was measured on various batches, the results are summarized in table 4 below:

TABLE 4

| Batch No. | Appearance | Melting point | Purity |
|---|---|---|---|
| MC00III17 | White grains | 189° C. | 99.5% |
| DG00IV53 | White crystals | 191° C. | 100.7% |
| DG00IV42 | White crystals | 189° C. | 100.7% |
| DG00IV52 | Yellow-white flakes | 190° C. | 99.8% |
| MC00III11 | Yellow-white grains | 186° C. | 97.6% |
| MC99II159 | Yellow-white grains | 189° C. | 100.3% |
| DG01V21 | Beige-yellow grains | 188° C. | 97.4% |
| DG01V20.3 | Beige-yellow crystals | 191° C. | 96.7% |
| DG01V20.2 | Pink grains | 187° C. | 91.2% |

It is observed that the melting point of (E)-5-[2-(3,5-di-tert-butyl-4-hydroxyphenyl)vinyl]-3-methylisoxazole is in the range of 185-193° C.

Apart from batch DG01V20.2, all the batches have a purity greater than 95% regardless of the appearance of the powder.

2.2.2 TLC

The TLC analysis is carried out under the following conditions:

$F_{254}$ silica plate sample: 100 µl of solution at 0.4 mg/ml in MeOH control at 1%: 20 µl of solution at 0.02 mg/ml control at 5%: 100 µl of solution at 0.02 mg/ml focusing: MeOH elution: hexane 90/10 ethyl acetate migration: about 5 cm development: UV 254 nm and solution at 5% $FeCl_3$ in 0.5M HCl (EtOH at 95%)

results:

X 254 nm: (E)-5-[2-(3,5-di-tert-butyl-4-hydroxyphenyl) vinyl]-3-methylisoxazole has a spot of high intensity at Rf: 0.30. The product of degradation also has a spot at Rf: 0.34.

X Developing agent $FeCl_3$: An orange-brown spot is obtained for (E)-5-[2-(3,5-di-tert-butyl-4-hydroxy-phenyl) vinyl]-3-methylisoxazole at the same Rf on an orange-colored background for the plate.

2.2 Assay 2.3.1 Loss on Drying

The loss on drying makes it possible to determine the content of water and of organic solvent. It is determined on 1 g if possible in an oven at 100-105° C. for 3 h or until constant weight is obtained.

A weighed sample of the order of 1 g is introduced into a previously dried crystallizing dish, and then the latter is placed in an oven thermostated at 100-105° C. for 3 h. The crystallizing dish is allowed to cool in a desiccator to room temperature. The crystallizing dish is weighed and the loss is calculated as % by the following formula:

$$\text{Loss (\%)} = \frac{(W - m) \times 100}{W}$$

with W: weighed amount introduced
m: mass after heating in an oven 2.3.2 HPLC Assay Principle:

The isocratic HPLC technique allows the assay of (E)-5-[2-(3,5-di-tert-butyl-4-hydroxyphenyl)vinyl]-3-methylisoxazole under conditions of specificity in relation to the two synthesis precursors, to an unknown synthesis impurity and to the product of degradation by UV radiation.

Method:

The purity of (E)-5-[2-(3,5-di-tert-butyl-4-hydroxyphenyl)vinyl]-3-methylisoxazole is determined by isocratic HPLC by external calibration and expressed relative to the dry substance.

Procedure:

Materials:

Column: Lichrosphere C18, 5 µm, 100 A°, 125×4 mm+precolumn (4×4 mm)

Mobile phase: 250H20+750 MeOH(HPLC solvents)

Flow rate: 1 ml/min

Room temperature

Detector: 240 nm

Volume for injection: 25 µl

Integrator: ST=25 min, CS=2.5, SP=400, Noise=2, Sens=40, Att=4

Merck chain: L-6200A type pump

Injector AS-2000A type

Detector L-4250 type

Integrator D-2500 type

The (E)-5-[2-(3,5-di-tert-butyl-4-hydroxyphenyl)-vinyl]-3-methylisoxazole control was synthesized, purified and dried in the laboratory.

Results:

The HPLC analysis makes it possible to verify that the purity of the product obtained by the method according to the invention is greater than 98%.

The invention claimed is:

1. A method for synthesizing derivatives corresponding to formula (I):

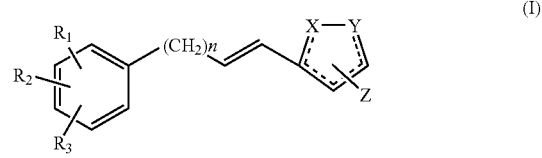

in which:

$R_1$, $R_2$, $R_3$, at the 2, 3, 4, 5 or 6 position of the phenyl ring, which are identical or different, are chosen from: a hydrogen atom; $C_1$-$C_6$ alkyls; $C_2$-$C_6$ alkenyls; $C_2$-$C_6$ alkynyls; halogens, $C_1$-$C_6$ haloalkyls; —OH; the groups —OR', —SH, —SR', —SeH, —SeR', —C(O)R', —NHC(O)R', —C(S)R', —NHC(S)R', —CN in which R' represents a group chosen from $C_1$-$C_6$ alkyls, $C_2$-$C_6$ alkenyls, $C_2$-$C_6$ alkynyls; the groups —C(O)OR", —OC(O)R", —NR"R'" in which R" and R'", which are identical or different, represent a group chosen from a hydrogen atom, $C_1$-$C_6$ alkyls, $C_2$-$C_6$ alkenyls, $C_2$-$C_6$ alkynyls;

X and Y represent a pair of atoms chosen from: (NR$_4$, N) (pyrazole ring), (O, N) (isoxazole ring), (S, N) (isothiazole ring), R$_4$ being chosen from: a hydrogen atom; C$_1$-C$_6$ alkyls; the groups CH$_2$—OR$_5$, the groups C(O)OR$_5$ in which R$_5$ is chosen from a hydrogen atom, a C$_1$-C$_6$ alkyl group, a benzyl group;

the heterocycle is linked to the phenyl ring via its 3- or 5-position in the case of the pyrazole ring, via its 5-position in the case of the isoxazole and isothiazole rings;

n represents an integer chosen from 0, 1, 2, 3, 4, 5 and 6;

Z, at the 3- or 4-position of the isoxazole, pyrazole or thioxazole ring, represents a group chosen from: a hydrogen atom; C$_1$-C$_6$ alkyls; C$_2$-C$_6$ alkenyls; C$_2$-C$_6$ alkynyls; halogens, C$_1$-C$_6$ haloalkyls; —OH; the groups —OR', —SH, —SR', —SeH, —SeR', —C(O)R', —NHC(O)R', —C(S)R', —NHC(S)R', —CN in which R' represents a group chosen from C$_1$-C$_6$ alkyls, C$_2$-C$_6$ alkenyls, C$_2$-C$_6$ alkynyls; the groups —C(O)OR'', —OC(O)R'', —NR''R''' in which R'' and R''', which are identical or different, represent a group chosen from a hydrogen atom, C$_1$-C$_6$ alkyls, C$_2$-C$_6$ alkenyls, C$_2$-C$_6$ alkynyls, this method being characterized in that it comprises at least one step consisting in treating the product corresponding to formula (II) below in which R$_1$, R$_2$, R$_3$, X, Y, Z and n have the same definition as in formula (I) above, in alcohol in the presence of a base to give the product of formula (I):

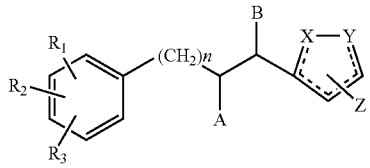

(II)

A and B being chosen such that one of A and B is H, the other being —OH.

2. The method as claimed in claim 1, characterized in that at least one of the conditions below is met:

R$_1$, R$_2$, R$_3$ are at the 3-, 4- or 5-position of the phenyl ring;

R$_1$, R$_2$, R$_3$ are chosen from: a hydrogen atom; C$_1$-C$_6$ alkyls; halogens; C$_1$-C$_6$ haloalkyls; —OH; the groups —OR', in which R' represents a group chosen from C$_1$-C$_6$ alkyls; the groups —OC(O)R'', in which R'' represents a group chosen from a hydrogen atom, C$_1$-C$_6$ alkyls;

X =O; Y =N;

n=0;

Z is at the 3-position of the heterocycle,

Z represents a group chosen from: C$_1$-C$_6$ alkyls; halogens; C$_1$-C$_6$ haloalkyls.

3. The method as claimed in claim 1, characterized in that the conditions below are met:

A=OH, B =H.

4. The method as claimed in claim 2, characterized in that at least one of the conditions below is met:

the heterocycle represented by formula:

is a Z-substituted derivative of 5-isoxazole;

R$_1$ at the 3-position is a tert-butyl group;

R$_2$ at the 4-position is a hydroxyl group;

R$_3$ at the 5-position is a tert-butyl group;

Z at the 3-position is a methyl group.

5. The method as claimed in claim 4, characterized in that the product (I) is (E)-5-[2-(3,5-di-tert-butyl-4-hydroxyphenyl)vinyl]-3-methylisoxazole.

6. The method as claimed in claim 1, characterized in that the alcohol in which the dehydration and the crystallization are performed is ethanol, methanol or isopropyl alcohol.

7. The method as claimed in claim 1, characterized in that the base which is added to the alcohol is sodium hydroxide in the form of an aqueous solution.

8. The method as claimed in claim 7, characterized in that the aqueous sodium hydroxide solution is a solution having a concentration of between 0.1 M and 5 M.

9. The method as claimed in claim 1, characterized in that it comprises the following steps: dissolution of the product (II) in alcohol under reflux; addition of the base until the compound (I) precipitates; addition of alcohol, still under reflux until the precipitate is solubilized; cooling of the solution which causes crystallization of(I); filtration and washing of the crystals.

10. The method as claimed in claim 1, comprising a step for preparing a compound of formula (II) in which A =OH and B =H, and in which X =O and Y =N, characterized in that the aldehyde (III) and the lithium salt of the heterocycle (IVa) are reacted in order to obtain the derivative (IIa$_1$):

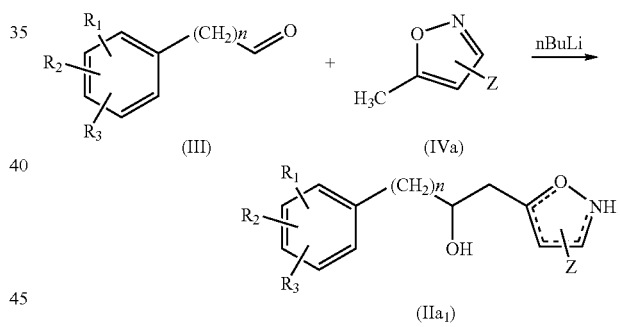

R$_1$, R$_2$, R$_3$ and Z having the same definition as in formula (II).

11. The method as claimed in claim 1, comprising a step for preparing a compound of formula (II) in which A =OH and B =H, and in which (X, Y) represents (S, N) or (NR$_4$, N), R$_4$ having the same definition as in formula (II), characterized in that a phenyloxirane (V) derivative is reacted with the lithium salt of the 5-isothiazole derivative (compound (TV) with X=S and Y=N) or with the lithium salt of the 5-pyrazole derivative (compound (IV) with (X, Y)= (NR$_4$, N)), according to the scheme below:

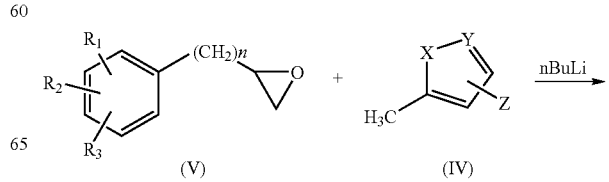

-continued
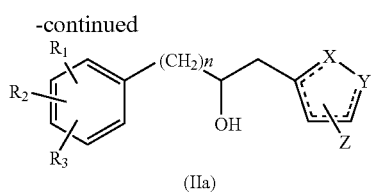
(IIa)
12. The method as claimed in claim 8, wherein the aqueous sodium hydroxide solution has a concentration of between 0.5M and 4M.
13. The method as claimed in claim 8, wherein the aqueous sodium hydroxide solution has a concentration of between 1M and 3M.
* * * * *